(12) United States Patent
Chen et al.

(10) Patent No.: US 6,766,680 B2
(45) Date of Patent: Jul. 27, 2004

(54) DETERMINATION OF GAS SOLUBILITY, ENTRAINED GAS CONTENT, AND TRUE LIQUID DENSITY IN MANUFACTURING PROCESSES

(75) Inventors: Qingyuan Chen, Appleton, WI (US); Robert Josef Franda, Sherwood, WI (US)

(73) Assignee: Appleton Papers, Inc., Appleton, WI (US)

( * ) Notice: Subject to any disclaimer, the term of this patent is extended or adjusted under 35 U.S.C. 154(b) by 75 days.

(21) Appl. No.: 10/046,240

(22) Filed: Jan. 16, 2002

(65) Prior Publication Data

US 2003/0131652 A1 Jul. 17, 2003

(51) Int. Cl.[7] ............................. G01N 5/00; G01N 7/00; G01N 37/00
(52) U.S. Cl. ...................... 73/19.05; 73/19.01; 73/19.1; 73/23.33; 73/25.04; 73/29.01
(58) Field of Search ........................... 73/19.01, 19.02, 73/19.03, 19.04, 19.05, 19.06, 19.09, 19.1, 19.11, 23.33, 25.04, 28.01, 29.01, 30.01, 31.01, 61.44

(56) References Cited

U.S. PATENT DOCUMENTS

| | | | | |
|---|---|---|---|---|
| 3,731,530 A | * | 5/1973 | Tanguy et al. | 73/152.42 |
| 3,939,693 A | * | 2/1976 | Dumont | 73/19.05 |
| 4,056,002 A | * | 11/1977 | Arieh et al. | 73/861.04 |
| 4,168,624 A | * | 9/1979 | Pichon | 73/195 |
| 4,516,580 A | * | 5/1985 | Polanyi | 600/364 |
| 4,584,866 A | * | 4/1986 | Janssen | 73/19.1 |
| 4,862,729 A | * | 9/1989 | Toda et al. | 73/19.05 |
| 4,924,695 A | * | 5/1990 | Kolpak | 73/19.01 |
| 5,041,990 A | * | 8/1991 | Yabumoto et al. | 702/24 |
| 5,365,435 A | | 11/1994 | Stephenson | 364/420 |
| 5,635,631 A | * | 6/1997 | Yesudas et al. | 73/61.46 |
| 5,846,831 A | * | 12/1998 | Silvis | 436/55 |
| 6,393,893 B1 | * | 5/2002 | Fetz et al. | 73/19.01 |
| 6,496,781 B1 | * | 12/2002 | Chen et al. | 702/25 |
| 2003/0051531 A1 | * | 3/2003 | Patashnick et al. | 73/28.01 |

OTHER PUBLICATIONS

Bergman et al., "On–Line Measurement of Coating Color Quality in Coater Supply System", 1999 TAPPI Coating Conference, Toronto, Canada, 1999 (16 pages).

Mütek News, No. 7, Aug. 2001 (4 pages).

Pulse)))) Air_V3, www.papec.com, Dec. 21, 2001 (3 pages).

Anton Paar, "On–line CO2 measurement in the beer and soft drink industry", Press Release, Jul. 2001 (3 pages).

\* cited by examiner

*Primary Examiner*—Herzon E. Williams
*Assistant Examiner*—David A. Rogers
(74) *Attorney, Agent, or Firm*—Birch, Stewart, Kolasch & Birch, LLP (57) ABSTRACT

Improved control of continuous processes that handle liquids. Data generated by this invention is used to control gas contents of liquids within optimum ranges, for instance in paper coating processes and in the manufacture of food products (ketchup), personal care products (shampoo), paints, and in any industry where information on entrained and/or dissolved gases, and related parameters such as true density of and gas solubility in process liquids, is employed to optimize processing. The amount of gas in a liquid is determined by subjecting a mixture of an incompressible liquid sample and a compressible gas to three or more different equilibrium pressure states, measuring the temperature and volume of the mixture at each of the pressure states, determining the changes in volume of the mixture between at least two different pairs of pressure states, and calculating the amount of gas in the liquid sample. The inventive apparatus includes: a reservoir for process fluid; piping through which fluid may be pumped, the piping being under the control of a pressure regulator which is capable of setting at least three different pressures P1, P2, and P3 in the apparatus; at least three fluid control valves V1, V2, and V3; a pressure gauge; a temperature gauge; and a density gauge.

15 Claims, 5 Drawing Sheets

One hardware system for indirect measurement method.

Figure 1: One hardware system for indirect measurement method.

Figure 2: Coating Application system.

Figure 3: Application of system to a Fruit Canning line.

Figure 4: One hardware system for direct measurement method, with the measurement sequence being P1>P2>P3, or P1<P2 and P1>P3, or any other feasible combinations Figure 5: Curtain coater application with deaeration system.

US 6,766,680 B2

DETERMINATION OF GAS SOLUBILITY, ENTRAINED GAS CONTENT, AND TRUE LIQUID DENSITY IN MANUFACTURING PROCESSES

FIELD OF THE INVENTION

This invention provides means for improving control of continuous processes that handle liquids, and therefore provides benefits to manufacturers by enabling them to effectively monitor and operate their processes. Data generated by this invention can be used to control the gas contents of liquids within optimum ranges, for instance in paper coating processes and in the manufacture of such products as food products (ketchup, mayonnaise, syrup), personal care products (skin cream, shampoo), pharmaceutical products, paints, petroleum blends, and the like. This invention is useful in any industry where information on entrained and/or dissolved air and other gases, and related parameters such as true density of and gas solubility in process liquids, is employed to optimize processing.

BACKGROUND OF THE INVENTION

Those skilled in the arts of processing liquids desire to know how much air and/or other gases are entrapped and dissolved therein for a variety of reasons. Entrapped air can cause undesired foaming during processing, e.g. in papermaking and in the preparation of foodstuffs, and can result in disruption of film products, e.g. from paints. Entrained gases distort such processing parameters as density, making precise control of processes impossible. Those skilled in the art know that, generally, the more viscous a fluid being processed, the more difficult it is for any entrained air to escape from it and consequently the greater the amount of air bubbles likely to be accumulated therein. Also, as pressure on a fluid is lowered, dissolved air or other gas therein tends to leave solution and form bubbles in the fluid.

There are a number of instruments that are currently commercially available for measuring the air or gas content in a liquid. Such instruments include Valmet's COLORMAT, Mütek's GAS-60, Papec's PULSE))))AIR, Capella Technology's CAPTAIR, Anton-Paar's CARBO 2100 $CO_2$ analyzer, and CyberMetrics' AIR TESTER.

Mütek's GAS-60, for instance, is said to be useful in the context of minimizing pinholes (voids) in papermaking processes. Pinholes develop when pressure is reduced and dissolved gases—which accumulate in the papermaking process due to mechanical effects and chemical and biological reactions—are released. The GAS 60 is installed on line and is used to determine the gas content of entrained and dissolved gases in pulp suspensions. Having determined gas content, process engineers are able to calculate how much (expensive) deaerating additive should be used, and thus to avoid unnecessarily increased manufacturing costs due to employing too much deaerating additive.

Papec's PULSE))))AIR__V3 is a sensor for the measurement of entrained air and gases in process fluids. It is said to be useful in the pulp and paper industry in connection with machine headboxes and white water systems, coatings, and brownstock washers, in the secondary fiber industry (for effluent treatment), in the paint industry, in oil bottling processes, in the processing of well drilling muds, and in general in any application needing entrained air information.

Anton-Paar's CARBO 2100 $CO_2$ analyzer employs a patented impeller method which is said to make it significantly faster that other commercially available systems for measuring and monitoring tasks and also for regulating the $CO_2$ content of process liquids during production runs in the beer and soft drink industry.

It is believed that all of these instruments adopt a common approach, using Boyle's Law. Boyle's law is given by the formula $$P_1 V_1 = P_2 V_2 \quad (1)$$

where $V_1$ and $V_2$ are the volumes of the free gas in the liquid at two different pressures, $P_1$ and $P_2$, respectively. Being a "two-point measurement", this common approach measures the volume difference $\Delta V = V_1 - V_2$ between $P_1$ and $P_2$, and calculates the volumes of free gas, $V_1$ and $V_2$, from Boyle's Law as $$V_1 = \frac{P_2 \Delta V}{P_2 - P_1} \text{ and } V_2 = \frac{P_1 \Delta V}{P_2 - P_1} \quad (2)$$

More general formulas, which correlate the volumes of free gas with the pressures being acted upon, can be derived from the Ideal Gas Law as $$P_1 V_1 = n_1 R T_1 \quad (3)$$

and $$P_2 V_2 = n_2 R T_2 \quad (4)$$

where R is the gas constant, and $n_1$, $T_1$ and $n_2$, $T_2$ are moles of free gas and temperatures at $P_1$ and $P_2$, respectively. In the case of $n_1 = n_2$ and $T_1 = T_2$, equations (3) and (4) can be simplified to the equation of Boyle's Law given in (1). Hence, Boyle's Law is, in fact, a special case of the Ideal Gas Law and is valid only if the moles of free gas and temperatures at $P_1$ and $P_2$ are kept constant.

In practice, a portion of free gas, however, will be dissolved into the liquid. The solubility of gas is, as a general rule, proportional to the gas pressure as stated in Henry's Law $$P = H n_d \quad (5)$$

where P, H, $n_d$ are the pressure of the gas being dissolved, the constant of Henry's Law, and moles of dissolved gas, respectively. This unquestionably makes $n_1 \neq n_2$ between $P_1$ and $P_2$, causing a violation of Boyle's Law. Therefore, using Boyle's Law for a "two-point measurement" is an unreliable approximation and can cause a significant amount of error, especially when the pressure difference between the two points becomes large.

To cure this error, there have been some attempts to use Henry's Law to compensate for the amount of the dissolved gas. This approach, however, is generally impractical, inasmuch as the constants of Henry's Law are not available for many process liquids, particularly for those containing multiple-components such as coating slurries. Using the known constant of one liquid to approximate the constant of the others may potentially introduce a considerable amount of error, because the solubility of gases such as air changes dramatically from liquid to liquid. The solubility of air in isooctane at standard temperature and pressure, for example, is more than 100 times higher than the solubility of air in water.

SUMMARY OF THE INVENTION

The present invention provides methods and apparatuses for determining the entrained gas content and/or the dissolved gas content of liquids. This invention provides means for improving control of continuous processes that handle liquids, and therefore provides benefits to manufacturers by enabling them to effectively monitor and operate their processes. Data generated by this invention can be used for instance to control the gas contents of liquids within optimum ranges, for instance in the processing of foam such as shaving cream or ice cream and to minimize gas contents, for instance in paper coating processes and in the manufacture of such products as food products (ketchup, mayonnaise, syrups, various sauces), personal care products (skin cream, shampoo, lotions, toothpaste), pharmaceutical products, herbicides, paints, lubricating greases, petroleum blends, water softeners, and the like. This invention is useful in any industry where information on entrained and/or dissolved gas, and related parameters such as true density and solubility of process liquids, is employed.

In one embodiment, this invention provides a method for controlling the entrained gas content of a liquid or slurry being flow-processed. The liquid or slurry being flow-processed may be—without limitation—a slurry of kaolin clay, calcium carbonate, titanium dioxide, or alumina trihydrate being supplied as a coating to a paper substrate. Alternatively—again without limitation—the liquid or slurry being flow-processed is ointment, cream, lotion, toothpaste, mayonnaise, ketchup, or lubricating grease being packaged into a retail container. The method comprises: a.) setting a quantitative target for the free gas content of said liquid or slurry; b.) continuously flowing said liquid or slurry and mixing an antifoam agent therewith; c.) determining the volume percentage of free gas, x %, from the formula $$x\% = \frac{V_s}{V_s + V}$$

wherein Vs is the volume of free gas under standard conditions and V is the gas-free volume of the liquid carrier component; e.) comparing the calculated free gas content to the target free gas content; and, f.) if the calculated free gas content is greater than the target free gas content, raising the amount of antifoam agent mixed in step b.).

In another embodiment, this invention provides an apparatus comprising a reservoir for process fluid, piping through which the process fluid may be pumped, and a deaerator unit, the improvement which comprises locating means for detecting the volume percentage of free gas in the process fluid in working relationship to the deaerator unit. In this apparatus, a single such detection means may be located downstream of the deaerator unit and wherein the apparatus further comprises an alarm capable of signaling the presence in the process fluid of a volume percentage of free gas higher than a pre-specified level. Alternatively, the apparatus may include two such detection means located, respectively, upstream and downstream of the deaerator unit and the apparatus may further comprises a comparator capable of determining and indicating the magnitude of any difference in volume percentage of free gas in the process fluid upstream of and downstream of the deaerator unit.

Another embodiment of this invention is a method for determining the amount of gas in a liquid which comprises subjecting a mixture of an incompressible liquid sample and a compressible gas to at least three different equilibrium pressure states, measuring the temperature and volume of the mixture at each of the at least three pressure states, determining the changes in volume of the mixture between at least two different pairs of pressure states, and calculating the amount of gas in the liquid sample by using the equation $$x\% = \frac{V_s}{V_s + V}$$

wherein V is the volume of the gas-free liquid in a sample chamber at ambient pressure and $V_s$ is determined by the equation $$V_s = \frac{\Delta V_1 T_s}{T} \frac{P_1^2}{P_s(P_2 - P_1)} + \frac{\Delta V_2 T_s}{T} \frac{P_3(P_2 - P_1)}{P_s(P_3 - P_2)} + \frac{P_1 - P_s}{P_s} \left[ \frac{\Delta V_1 T_s}{T} - \frac{\Delta V_2 T_s}{T} \frac{P_3(P_2 - P_1)}{P_1(P_3 - P_2)} \right]$$

wherein $P_1$, $P_2$, and $P_3$ are three different equilibrium ambient pressures, $P_s$ and $T_s$ are standard pressure and temperature, $\Delta V_1$ and $\Delta V_2$ are the volume difference of the free air measured at an equilibrium state between $P_1$ and $P_2$ and $P_2$ and $P_3$, respectively. In preferred embodiments of this embodiment of the invention, the at least three equilibrium pressure states differ from one another at least to the extent that the three different volumes differ from one another by at least 0.1% and/or the at least three equilibrium pressure states differ from one another at least to the extent that three different apparent densities of said liquid differ from one another by at least 0.1%. In other preferred embodiments of this embodiment of the invention, the at least three pressure states differ from one another by at least 0.1 psi and/or the at least three pressure states differ from one another by at least 1 atmosphere. In this embodiment of the invention, the determination of changes in volume may be accomplished by measurement of volumes or by measurement of apparent densities.

The present invention also provides an apparatus that includes: a reservoir for process fluid; piping through which the fluid may be pumped, said piping being under the control of a pressure regulator which is capable of setting at least three different pressures P1, P2, and P3 in the apparatus; at least three fluid control valves V1, V2, and V3; a pressure gauge; a temperature gauge; and a density gauge. This apparatus may be used for obtaining data for use in determining amounts of air entrained or dissolved in a fluid, by a method that comprises: providing the apparatus as described; collecting stabilized pressure, temperature, and density data at a first pressure level; collecting stabilized pressure, temperature, and density data at a second pressure level; and collecting stabilized pressure, temperature, and density data at a third pressure level.

Yet another embodiment of this invention is a method for automatically controlling the output of a continuous process that requires mixing of a solid or liquid component with a liquid carrier component. This method embodiment of the invention comprises: a.) setting a quantitative target for weight-% of one or more solids and/or concentration of one or more liquids to the liquid carrier component; b.) continuously mixing said solids and/or liquids with the liquid carrier component; c.) filling a measurement chamber with the blended mixture and allowing it to come to equilibrium; d.) recording equilibrium temperature, $T_1$, the volume of the sample, $V_1$, and equilibrium pressure, $P_1$; e.) increasing or decreasing the volume of the mixture in the sample chamber, allowing the fluid to come to equilibrium, and recording equilibrium temperature, $T_2$, sample volume, $V_2$, and equilibrium pressure, $P_2$; f.) again, increasing or decreasing the volume of the mixture in the sample chamber, allowing the fluid to come to equilibrium, and recording equilibrium temperature, $T_3$, sample volume, $V_3$, and equilibrium pressure, $P_3$; g.) determining the true density, ρ, by employing the formula $$\rho = \frac{m}{V}$$

wherein the mass, m, is the mass of the liquid mixture sample, and, the gas-free volume of the liquid mixture, V, and the volume percentage of free air or other gas, x %, are calculated from the formulas $$V = V_{t1} - \left[\Delta V_1 \frac{P_1}{(P_2 - P_1)} + \Delta V_2 \frac{P_3(P_2 - P_1)}{P_1(P_3 - P_2)}\right]$$

and, $$x\% = \frac{V_s}{V_s + V}$$

wherein $\Delta V_1$ is the volume difference of the free gas between $P_1$ and $P_2$, $\Delta V_2$ is the volume difference of the free gas between $P_2$ and $P_3$, $V_{t1}$ is the total volume of the liquid and entrained gas, and Vs is the volume of free air or other gas under standard conditions and is calculated from the formula $$V_s = \frac{\Delta V_1 T_s}{T} \frac{P_1^2}{P_s(P_2 - P_1)} + \frac{\Delta V_2 T_s}{T} \frac{P_3(P_2 - P_1)}{P_s(P_3 - P_2)} + \frac{P_1 - P_s}{P_s}\left[\frac{\Delta V_1 T_s}{T} - \frac{\Delta V_2 T_s}{T} \frac{P_3(P_2 - P_1)}{P_1(P_3 - P_2)}\right]$$

wherein these variables are provided by the data collected in steps d.–f.), and standard conditions refer to $P=P_s=1$ atm, $T=T_s=273$ K; h.) calculating the weight-% of solids and/or the liquid concentration in the mixture with the equation $$m = \frac{1}{\left(1 - \rho_L \sum_{i=1}^n \frac{k_i x_i}{(\rho_s)_i}\right)} - \frac{\rho_L}{\left(1 - \rho_L \sum_{i=1}^n \frac{k_i x_i}{(\rho_s)_i}\right)}\left(\frac{1}{\rho}\right)$$

wherein $\rho_L$ is the density of the liquid carrier component, $k_i$ is the Additive Volume Coefficient (AVC) for each solid or liquid, $x_i$ is the weight-% dry for each solid or the concentration for each liquid, $(\rho_s)_i$ is the density of each solid or liquid, and $\rho$ is the true density of the mixture; i.) comparing the calculated weight-% solids or concentration to the target weight-% solids or concentration; and, j.) if the calculated weight-% solids or concentration is greater or less than the target weight-% solids or concentration, lowering or raising the amount of solids or liquids mixed in step b.).

Another inventive method for automatically controlling the output of a continuous process that requires mixing of a solid or liquid component with a liquid carrier component of this invention includes the steps of: a.) setting a quantitative target for weight-% of one or more solids and/or concentration of one or more liquids to the liquid carrier component; b.) continuously mixing said solids and/or liquids with the liquid carrier component; c.) diverting a fluid sample from the main piping system into the sample measurement chamber and allowing the sample to come to equilibrium; d.) recording equilibrium temperature, $T_1$, equilibrium density, $\rho_1$, and equilibrium pressure, $P_1$; e.) adjusting the pressure of the fluid in the sample chamber, allowing the fluid to come to equilibrium, and recording equilibrium temperature, $T_2$, equilibrium density, $\rho_2$, and equilibrium pressure, $P_2$; f.) again, adjusting the pressure of the fluid in the sample chamber, allowing the fluid to come to equilibrium, and recording equilibrium temperature, $T_3$, equilibrium density, $\rho_3$, and equilibrium pressure, $P_3$; g.) determining the true density, $\rho$, by employing the formula $$\rho = \frac{1}{V}$$

wherein the volume, V, is calculated from the formula $$V = \frac{1}{\rho_1} - \left[\left(\frac{1}{\rho_1} - \frac{1}{\rho_2}\right)\frac{P_1}{(P_2 - P_1)} + \left(\frac{1}{\rho_2} - \frac{1}{\rho_3}\right)\frac{P_3(P_2 - P_1)}{P_1(P_3 - P_2)}\right]$$

wherein these variables are provided by the data collected in steps d.–f.); h.) calculating the weight-% of solids and/or the liquid concentration in the mixture with the equation $$m = \frac{1}{\left(1 - \rho_L \sum_{i=1}^n \frac{k_i x_i}{(\rho_s)_i}\right)} - \frac{\rho_L}{\left(1 - \rho_L \sum_{i=1}^n \frac{k_i x_i}{(\rho_s)_i}\right)}\left(\frac{1}{\rho}\right)$$

wherein $\rho_L$ is the density of the liquid carrier component, $k_i$ is the Additive Volume Coefficient (AVC) for each solid or liquid, $x_i$ is the weight-% dry for each solid or the concentration for each liquid, $(\rho_s)_i$ is the density of each solid or liquid, and $\rho$ is the true density of the mixture; i.) comparing the calculated weight-% solids or concentration to the target weight-% solids or concentration; and, j.) if the calculated weight-% solids or concentration is greater or less than the target weight-% solids or concentration, lowering or raising the amount of solids or liquids mixed in step b.).

Both of these two methods of this invention can be used in a process for continuously coating a substrate, for instance where the substrate is a paper web and the solids component comprises kaolin clay, calcium carbonate, titanium dioxide, or alumina trihydrate, in a method that comprises: a.) setting a quantitative target for weight-% of one or more solids to be coated onto a substrate; b.) continuously applying the solids to the substrate via a carrier fluid; c.) measuring the apparent density of the slurry; d.) determining the true density of the slurry; e.) calculating the weight-% of solids in the slurry in the manner either of the former or the latter general method; f.) comparing the calculated weight-% solids to the target weight-% solids; and, g.) if the calculated weight-% is greater or less than the target weight-%, lowering or raising the amount of solids applied in step b.).

Likewise, either of these two general methods of this invention can be used in a process for controlling the output of a continuous process for preparing a syrup. This method comprises: a.) setting a quantitative target for a concentration of one or more carbohydrates, e.g. sucrose, and/or carbohydrate-containing liquids, e.g. corn syrup and high fructose corn syrup, to be blended, along with water, into a syrup; b.) continuously supplying the carbohydrate and/or carbohydrate-containing liquid and a dilution liquid to a vessel and mixing said liquids to form a slurry; c.) measuring the apparent density of the slurry; d.) determining the true density of the slurry; e.) converting this true density to the calculated carbohydrate concentration; f.) comparing the calculated carbohydrate concentration to the target carbohydrate concentration; and, g.) if the calculated carbohydrate concentration is greater or less than the target carbohydrate concentration, lowering or raising the amount of carbohydrates and/or volume of carbohydrate-containing liquids supplied in step b.).

In a third group of practical applications, this invention provides a method for controlling the output of a continuous process for preparing a carbonated beverage, e.g. a soft drink, beer, or a carbonated wine. This method comprises: a.) setting a quantitative target for a concentration of carbon dioxide to be blended into an aqueous medium; b.) continuously supplying carbon dioxide to the aqueous medium in a vessel and mixing those components to form a carbonated aqueous medium in the vessel at a preset "bottling" pressure $P_0$, wherein $P_0$ is the produced "bottling" pressure inside a sealed carbonated beverage container, at which pressure all of the free carbon dioxide is dissolved into the aqueous medium; c.) diverting a carbonated aqueous medium sample from the vessel into a sample measurement chamber at the same "bottling" pressure $P_0$; d.) reducing the aqueous medium pressure from $P_0$ to $P_1$ allowing the dissolved carbon dioxide to start to be released back to the aqueous medium in a free-bubble form; e.] reducing the aqueous medium pressure further from $P_1$ to $P_2$ allowing a sufficient amount of the dissolved carbon dioxide to be released back to the aqueous medium in a free-bubble form; f.) measuring the change in volume of the carbon dioxide liquid mixture at an equilibrium state between $P_1$ and $P_2$; g.) reducing the aqueous medium pressure further from $P_2$ to $P_3$ allowing more dissolved carbon dioxide to be released back to the aqueous medium in a free-bubble form; h.) measuring the change in volume of the carbon dioxide liquid mixture at an equilibrium state between $P_2$ and $P_3$; i.) determining the volume of free carbon dioxide, $V_s$, in the carbonated aqueous medium at the standard condition using the equation $$V_s = \frac{\Delta V_1 T_s}{T} \frac{P_1^2}{P_s(P_2 - P_1)} + \frac{\Delta V_2 T_s}{T} \frac{P_3(P_2 - P_1)}{P_s(P_3 - P_2)} + \frac{P_1 - P_s}{P_s}\left[\frac{\Delta V_1 T_s}{T} - \frac{\Delta V_2 T_s}{T} \frac{P_3(P_2 - P_1)}{P_1(P_3 - P_2)}\right]$$

wherein $P_1$, $P_2$, and $P_3$ are three different equilibrium ambient pressures, $P_s$ and $T_s$ are standard pressure and temperature, $\Delta V_1$, and $\Delta V_2$ are the volume difference of the free carbon dioxide measured at an equilibrium state between $P_1$ and $P_2$ and $P_2$ and $P_3$, respectively; j.] calculating the carbon dioxide concentration using the equation $$x\% = \frac{V_s}{V_s + V}$$

wherein $V_s$ is the volume of free carbon dioxide determined in i.] and V is the volume of carbonated aqueous medium in the sample chamber at a preset "bottling" pressure $P_0$ upon which no free bubble should present; k.) comparing the calculated carbon dioxide concentration to the target carbon dioxide concentration; and, l.) if the calculated carbon dioxide concentration is greater or less than the target carbon dioxide concentration, lowering or raising the volume of carbon dioxide supplied in step b.).

This invention also provides various analytical methods. One is a method for determining the concentration of a solid or liquid component in a liquid carrier component, which comprises measuring the apparent density of the mixture; determining therefrom the true density of the mixture; and calculating the weight-% of solids in the slurry in the manner taught above. Another is a method for determining the true density of a solid or liquid component in a liquid carrier component, which comprises measuring the apparent density of the mixture; and determining therefrom the true density of the mixture. Another is a method for determining the entrained air content of a liquid component, which comprises measuring the apparent air content of the liquid at a variety of pressures; and determining therefrom the true entrained air content of the liquid. Another is a method of characterizing a liquid by determining its entrained air content, which comprises calculating the volume percentage of free air, x %, in the liquid using the equation $$x\% = \frac{V_s}{V_s + V}$$

wherein V is the volume of the gas-free liquid in a sample chamber at ambient pressure and $V_s$ is determined by the equation $$V_s = \frac{\Delta V_1 T_s}{T} \frac{P_1^2}{P_s(P_2 - P_1)} + \frac{\Delta V_2 T_s}{T} \frac{P_3(P_2 - P_1)}{P_s(P_3 - P_2)} + \frac{P_1 - P_s}{P_s}\left[\frac{\Delta V_1 T_s}{T} - \frac{\Delta V_2 T_s}{T} \frac{P_3(P_2 - P_1)}{P_1(P_3 - P_2)}\right]$$

wherein $P_1$, $P_2$, and $P_3$ are three different equilibrium ambient pressures, $P_s$ and $T_s$ are standard pressure and temperature, $\Delta V_1$ and $\Delta V_2$ are the volume difference of the free air measured at an equilibrium state between $P_1$ and $P_2$ and $P_2$ and $P_3$, respectively.

Finally, this invention provides various methods of identifying samples of unknown constitution. One such method comprises comparing its entrained air content with a collection of entrained air contents, for a variety of known compounds, determined in the manner taught above. Another comprises comparing its true density with a collection of true densities, for a variety of known compounds, determined by use of the relationship $$\rho = \frac{m}{V}.$$

Another comprises comparing its % solids with a collection of % solids, for a variety of known compounds, determined according to the relationship $$m = \frac{1}{\left(1 - \rho_L \sum_{i=1}^{n} \frac{k_i x_i}{(\rho_S)_i}\right)} - \frac{\rho_L}{\left(1 - \rho_L \sum_{i=1}^{n} \frac{k_i x_i}{(\rho_S)_i}\right)}\left(\frac{1}{\rho}\right).$$

BRIEF DESCRIPTION OF THE DRAWINGS

The present invention will be more fully understood from the detailed description given hereinbelow and from the accompanying drawings. These drawings are provided by way of illustration only, and thus do not in any way limit the present invention. In particular, it is noted that the hardware configurations depicted in these drawings are illustrative only (and not to scale). Those skilled in the art can easily develop alternative hardware configurations that will likewise obtain the benefits of the present invention.

DETAILED DESCRIPTION OF THE INVENTION

The following symbols are used from Equation [1] through [38]:

$P_1$, $P_2$, $P_3$: Different equilibrium ambient pressures measured by a pressure sensor
P: Pressure of the gas being dissolved
$V_1$, $V_2$, $V_3$: Volumes of the free gas entrained into a liquid at $P_1$, $P_2$, and $P_3$, respectively
$n_1$, $n_2$, $n_3$: Moles of the free gas entrained into a liquid at $P_1$, $P_2$, and $P_3$, respectively
$\rho_1$, $\rho_2$, $\rho_3$: Equilibrium apparent densities of the liquid that contains entrained gas being measured at $P_1$, $P_2$, and $P_3$, respectively
$\rho$: Gas-free true density of the liquid
V: Gas-free volume of the liquid
$V_{t1}$: Total volume of the liquid that contains entrained gas being measured at $P_1$
$\Delta V_1$: The volume difference of the free gas measured at an equilibrium state between $P_1$ and $P_2$ (a measurable value)
$\Delta V_2$: The volume difference of the free gas measured at an equilibrium state between $P_2$ and $P_3$ (a measurable value)
R: The constant of the Ideal Gas Law
T: Equilibrium temperature of the process liquid/solution measured by a temperature sensor, assuming that the temperature is kept constant between the three measurement points (T=$T_1$=$T_2$=$T_3$)
H: The constant of Henry's Law
$n^*$: Moles of the dissolved gas at $P_1$
$n_d$: Moles of the dissolved gas at P
$n'_1$, $n'_2$, $n'_3$: Moles of the normalized free gas at $P_1$, $P_2$, and $P_3$, respectively (with $n^*$ being neglected for the purpose of solving the constant of Henry's Law explicitly)
$P_g$: Gas pressure inside the entrained gas bubbles
$\sigma$: Liquid surface tension
r: The medium radius of the entrained gas bubbles
$P_s$, $T_s$: Atmospheric pressure, $P_s$=1 atm (14.7 psi) and standard temperature, $T_s$=25° C.
$n_s$, $V_s$: Moles and volume of free gas at $P_s$ and $T_s$
x %: Volume percentage of free gas at $P_s$ and $T_s$
$m_{pyc}$: Mass of the liquid mixture sample collected by a pycnometer
$V_{pyc}$: Volume of the pycnometer
m: Mass of the liquid mixture sample The following key equations are used in this application:

H: Henry's Law constant.

$$H = \left[\frac{\Delta V_1}{RT} - \frac{\Delta V_2}{RT}\frac{P_3(P_2 - P_1)}{P_1(P_3 - P_2)}\right]^{-1} \quad (25)$$

Usage: determining the solubility, in terms of the magnitude of H, for one specific gas dissolved into different liquids or for different gases dissolved into one specific liquid; calculating the amount of dissolved gas using Henry's law P H$n_d$ (Equation [5]) at a specific pressure, P.
Applied Method: direct measurement. For an indirect measurement, $$\Delta V_1 = \frac{1}{\rho_1} - \frac{1}{\rho_2}$$

and $$\Delta V_2 = \frac{1}{\rho_2} - \frac{1}{\rho_3}$$

are needed to be substituted into [25].
V: gas-free volume of the liquid mixture being measured.

$$V = V_{tl} - \left[\Delta V_1 \frac{P_1}{(P_2 - P_1)} + \Delta V_2 \frac{P_3(P_2 - P_1)}{P_1(P_3 - P_2)}\right] \quad (30)$$

Usage: being a parameter used in [34] for determining the volume percentage of free gas, x %, at standard pressure and temperature (this parameter can be used in a similar formula for determining the volume percentage of free gas at other pressures as well); being a parameter used in [35] for determining the true density of the gas-free liquid.
Applied Method: direct measurement.
$V_s$: the volume of free gas at the atmospheric pressure.

$$V_s = \frac{\Delta V_1 T_s}{T} \frac{P_1^2}{P_s(P_2 - P_1)} + \frac{\Delta V_2 T_s}{T} \frac{P_3(P_2 - P_1)}{P_s(P_3 - P_2)} + \frac{P_1 - P_s}{P_s}\left[\frac{\Delta V_1 T_s}{T} - \frac{\Delta V_2 T_s}{T}\frac{P_3(P_2 - P_1)}{P_1(P_3 - P_2)}\right] \quad (33)$$

Usage: converting the volume of free gas from one specific pressure to that at the atmospheric pressure, which can further be used in [34] for determining the volume percentage of free gas, x %, at the standard condition.
Applied Method: direct measurement.
x %: volume percentage of free gas at standard pressure and temperature.

$$x\% = \frac{V_s}{V_s + V} \quad (34)$$

Usage: determining the volume percentage of free gas, x %, at the standard condition.
Applied Method(s): both direct and indirect measurements.
$\rho$: true density of gas-free liquid.

$$\rho = \frac{m_{pyc}}{x\% V_{pyc}} \quad (35\text{-A})$$

Usage: calculating the true density of gas-free liquid using a pycnometer preferably in a lab scenario, which can further be used as a reliable basis for determining % solids.
Applied Method: direct measurement (lab method).
$\rho$: true density of gas-free liquid.

$$\rho = \frac{m}{V} \quad [35\text{-B}]$$

Usage: calculating the true density of gas-free liquid in a production environment scenario, which can further be used as a reliable basis for determining % solids.
Applied Method: direct measurement.
V: gas-free volume of the liquid in 1 unit of mass of liquid mixture.

$$V = \frac{1}{\frac{1}{\rho_1} - V_1} = \frac{1}{\rho_1} - \left[\left(\frac{1}{\rho_1} - \frac{1}{\rho_2}\right)\frac{P_1}{(P_2-P_1)} + \left(\frac{1}{\rho_2} - \frac{1}{\rho_3}\right)\frac{P_3(P_2-P_1)}{P_1(P_3-P_2)}\right] \quad (36)$$

Usage: being a parameter used in [34] for determining the volume percentage of free gas, x %, at standard pressure and temperature (this parameter can be used in a similar formula for determining the volume percentage of free gas at other pressures as well); being a parameter used in [37] for determining the true density of the gas-free liquid.
Applied Method: indirect measurement.
ρ: true density of gas-free liquid.

$$\rho = \frac{1}{V} \quad (37)$$

Usage: calculating the true density of gas-free liquid in 1 unit of mass of liquid mixture, which can further be used as a reliable basis for determining % solids.
Applied Method: indirect measurement.
$V_s$: the volume of free gas at the atmospheric pressure.

$$V_s = \left(\frac{1}{\rho_1} - \frac{1}{\rho_2}\right)\frac{T_s}{T}\frac{P_1^2}{P_s(P_2-P_1)} + \left(\frac{1}{\rho_2} - \frac{1}{\rho_3}\right)\frac{T_s}{T}\frac{P_3(P_2-P_1)}{P_s(P_3-P_2)} + \frac{P_1-P_s}{P_s}\left[\left(\frac{1}{\rho_1} - \frac{1}{\rho_2}\right)\frac{T_s}{T} - \left(\frac{1}{\rho_2} - \frac{1}{\rho_3}\right)\frac{T_s}{T}\frac{P_3(P_2-P_1)}{P_1(P_3-P_2)}\right] \quad (38)$$

Usage: converting the volume of free gas from one specific pressure to that at the atmospheric pressure, which can further be used in [34] for determining the volume percentage of free gas, x %, at the standard condition.
Applied Method: indirect measurement.

In the disclosure that follows, every measured parameter, pressure, apparent density, temperature, and change in volume should be understood to be an equilibrium value.

The relationship between the gas pressure, $P_g$, inside gas bubbles entrained in a liquid and ambient pressure, P, in equilibrium can be expressed (according to the Young-Laplace Equation) as $$P_g = P + \frac{2\sigma}{r} \quad (6)$$

If the size of the entrained gas bubbles is sufficiently large, the second item in (6) will be relatively small and insignificant, e.g., $$\frac{2\sigma}{r} \leq 0.1$$

atm (1.4 psi) when r≧1 mm (0.079"). The gas pressure, $P_g$, inside the gas bubbles can then be replaced by the ambient pressure, P, with a sufficiently high accuracy.

Under these circumstances, the ambient pressure can consequently be substituted into the ideal gas law PV=nRT, giving the volumes of free gas in a liquid at different pressures $$V_1 = \frac{n_1 RT}{P_1} \quad (7)$$

$$V_2 = \frac{n_2 RT}{P_2} \quad (8)$$

$$V_3 = \frac{n_3 RT}{P_3} \quad (9)$$

NOTE: assuming $T=T_1=T_2=T_3$

The volume differences, $\Delta V_1$ and $\Delta V_2$, between $P_1-P_2$ and $P_2-P_3$ are the reflection of the change in volume of the entrained gas only, since the liquid itself is incompressible. Equations (7), (8), and (9) can therefore be combined to $$V_1 - V_2 = \Delta V_1 = \left(\frac{n_1}{P_1} - \frac{n_2}{P_2}\right)RT \quad (10)$$

$$V_2 - V_3 = \Delta V_2 = \left(\frac{n_2}{P_2} - \frac{n_3}{P_3}\right)RT \quad (11)$$

$\Delta V_1$ and $\Delta V_2$, in general, can be determined either DIRECTLY by measuring the changes in volume; or INDIRECTLY by measuring the changes in apparent density.

By assuming that the unit of mass equals 1, the relationships between these two options can readily be found as $$\Delta V_1 = \frac{1}{\rho_1} - \frac{1}{\rho_2} \quad (12)$$

$$\Delta V_2 = \frac{1}{\rho_2} - \frac{1}{\rho_3} \quad (13)$$

Equations (10) and (11) can be rewritten as $$P_2 n_1 - P_1 n_2 = \frac{1}{RT}\Delta V_1 P_1 P_2 \quad (14)$$

$$P_3 n_2 - P_2 n_3 = \frac{1}{RT}\Delta V_2 P_2 P_3 \quad (15)$$

In equilibrium, by applying Henry's Law, the amounts of the dissolved gas at $P_1$, $P_2$, and $P_3$, respectively, can be written as $$P_1 = Hn^* \quad (16)$$

$$P_2 = H[n^* + (n_1 - n_2)] \quad (17)$$

$$P_3 = H[n^* + (n_1 - n_3)] \quad (18)$$

Equations (14)–(18) are a group of underdetermined linear equations, which, in theory, have an infinite number of solutions. Such equations, nevertheless, have a unique solution if any one of the variables can be determined. For the purpose of determining the constant of Henry's Law, H, explicitly, it is arbitrarily to neglect n* at this moment. This would allow (17) and (18) to be simplified as $$P_2 = H(n'_1 - n'_2) \quad (19)$$

$$P_3 = H(n'_1 - n'_3) \quad (20)$$

or $$\frac{P_2}{P_3} = \frac{n'_1 - n'_2}{n'_1 - n'_3} \quad (21)$$

This manipulation actually assumes that the amount of the dissolved gas follows $P = H'(n - n^*)$ that has a curve with a slope being parallel to $P = Hn$. $n'_3$ can then be obtained from (21) as $$n'_3 = \frac{1}{P_2}[P_3 n'_2 - (P_3 - P_2) n'_1] \quad (22)$$

By substituting $n'_3$ back into (15), $n'_1$ can be solved as $$n'_1 = \frac{\Delta V_2}{RT} \frac{P_3 P_2}{P_3 - P_2} \quad (23)$$

Likewise, $n'_2$ can also be solved from (14)

$$n'_2 = \frac{\Delta V_2}{RT} \frac{P_3 P_2^2}{P_1(P_3 - P_2)} - \frac{\Delta V_1}{RT} P_2 \quad (24)$$

The constant of Henry's Law, H, can therefore be determined from (19)

$$H = \frac{P_2}{n'_1 - n'_2} = \left[\frac{\Delta V_1}{RT} - \frac{\Delta V_2}{RT} \frac{P_3(P_2 - P_1)}{P_1(P_3 - P_2)}\right]^{-1} \quad (25)$$

Let $P_1 \times [(17)-(16)]$ $$HP_1 n_1 - HP_1 n_2 = P_1(P_2 - P_1) \quad (26)$$

Let $H \times (14)$ $$HP_2 n_1 - HP_1 n_2 = \frac{H}{RT} \Delta V_1 P_1 P_2 \quad (27)$$

$n_1$ can finally be solved from (27)–(26), substituting (25) for H.

$$n_1 = \frac{\Delta V_1}{RT} \frac{P_1 P_2}{(P_2 - P_1)} - \frac{P_1}{H} \quad (28)$$

$$= \frac{\Delta V_1}{RT} \frac{P_1^2}{(P_2 - P_1)} + \frac{\Delta V_2}{RT} \frac{P_3(P_2 - P_1)}{(P_3 - P_2)}$$

The volume of free gas, $V_1$, at $P_1$ is then attainable $$V_1 = \frac{n_1 RT}{P_1} = \Delta V_1 \frac{P_1}{(P_2 - P_1)} + \Delta V_2 \frac{P_3(P_2 - P_1)}{P_1(P_3 - P_2)} \quad (29)$$

and the gas-free volume of the liquid, V, can also be determined $$V = V_{tl} - V_1 = V_{tl} - \left[\Delta V_1 \frac{P_1}{(P_2 - P_1)} + \Delta V_2 \frac{P_3(P_2 - P_1)}{P_1(P_3 - P_2)}\right] \quad (30)$$

To determine the moles of free gas, $n_s$, at the atmospheric pressure, $P_s$, the difference of dissolved gas, $\Delta n_s$, between $P_1$ and $P_s$ should first be calculated from Henry's Law $$\Delta n_s = \frac{1}{H}(P_1 - P_s) = (P_1 - P_s)\left[\frac{\Delta V_1}{RT} - \frac{\Delta V_2}{RT} \frac{P_3(P_2 - P_1)}{P_1(P_3 - P_2)}\right] \quad (31)$$

$n_s$ can then be expressed as $$n_s = n_1 + \Delta n_s = \frac{\Delta V_1}{RT} \frac{P_1^2}{(P_2 - P_1)} + \quad (32)$$

-continued $$\frac{\Delta V_2}{RT} \frac{P_3(P_2 - P_1)}{(P_3 - P_2)} +$$

$$(P_1 - P_s)\left[\frac{\Delta V_1}{RT} - \frac{\Delta V_2}{RT} \frac{P_3(P_2 - P_1)}{P_1(P_3 - P_2)}\right]$$

The volume of free gas, $V_s$, at the atmospheric pressure, $P_s$, is therefore $$V_s = \frac{n_s R T_s}{P_s} = \frac{\Delta V_1 T_s}{T} \frac{P_1^2}{P_s(P_2 - P_1)} + \quad (33)$$

$$\frac{\Delta V_2 T_s}{T} \frac{P_3(P_2 - P_1)}{P_s(P_3 - P_2)} +$$

$$\frac{P_1 - P_s}{P_s}\left[\frac{\Delta V_1 T_s}{T} - \frac{\Delta V_2 T_s}{T} \frac{P_3(P_2 - P_1)}{P_1(P_3 - P_2)}\right]$$

Alternatively, $V_s$ could be determined with the use of the Ideal Gas Law and equation (29), above $$V_s = \frac{T_s P_1 V_1}{T_1 P_s} \quad (33 \text{ bis})$$

The volume percentage of free gas, x %, at $P_s$ and $T_s$ can thus be attained as $$x\% = \frac{V_s}{V_s + V} \quad (34)$$

DIRECT MEASUREMENT (for true density). For a laboratory measurement, the gas-free true density, ρ, can be determined using a pycnometer, or a similar device. A pycnometer is a device for determining the specific gravity of liquids and solids. In this case, by weighing the mass, $m_{pyc}$, of the liquid mixture sample and dividing the known volume, $V_{pyc}$, of the pycnometer, the true density, ρ, turns out to be $$\rho = \frac{m_{pyc}}{x\% V_{pyc}} \quad (35)$$

Figure 4:
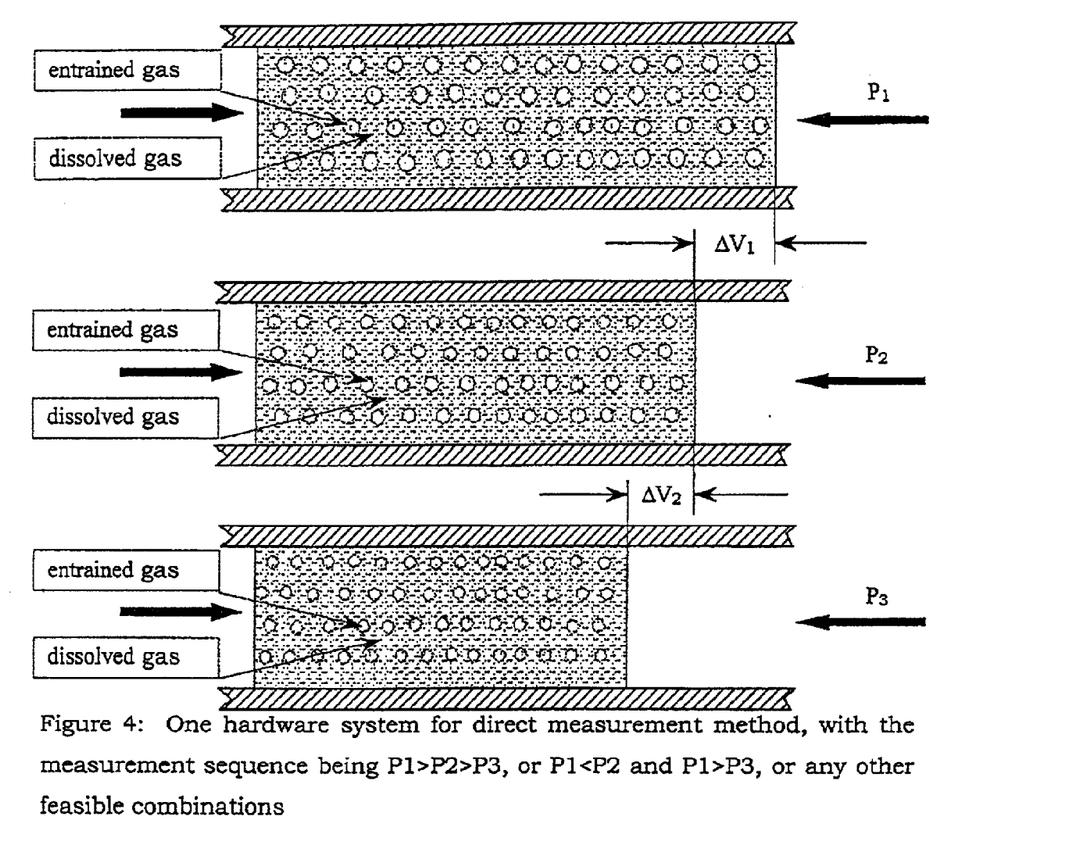
FIG. 4 is a schematic representation of a direct measurement apparatus embodiment of the present invention (measuring volume, e.g. using a piston in a cylinder).

Or, for an online application, these mass and volume measurements could be obtained by incorporating a load cell (a weight measurement instrument) into a controlled-volume sample chamber such as is demonstrated in FIG. 4. Such a device would provide a simple method of obtaining the data required to calculate percent entrained air, percent dissolved air, Henry's Law constant, and true density of a solution in real-time. In this application, true density would be determined via formula (35-B)

$$\rho = \frac{m}{V} \quad [35\text{-B}]$$

where m is the mass of the fluid in the sample chamber and V is the gas-free volume of the liquid.

INDIRECT MEASUREMENT (for true density). In case of the indirect measurement, the gas-free volume of the liquid, V, in 1 unit of mass of liquid mixture is $$V = \quad (36)$$

-continued $$\frac{1}{\rho_1} - V_1 = \frac{1}{\rho_1} - \left[\left(\frac{1}{\rho_1} - \frac{1}{\rho_2}\right)\frac{P_1}{(P_2 - P_1)} + \left(\frac{1}{\rho_2} - \frac{1}{\rho_3}\right)\frac{P_3(P_2 - P_1)}{P_1(P_3 - P_2)}\right]$$

and the true density is $$\rho = \frac{1}{V} \qquad (37)$$

Figure 1:
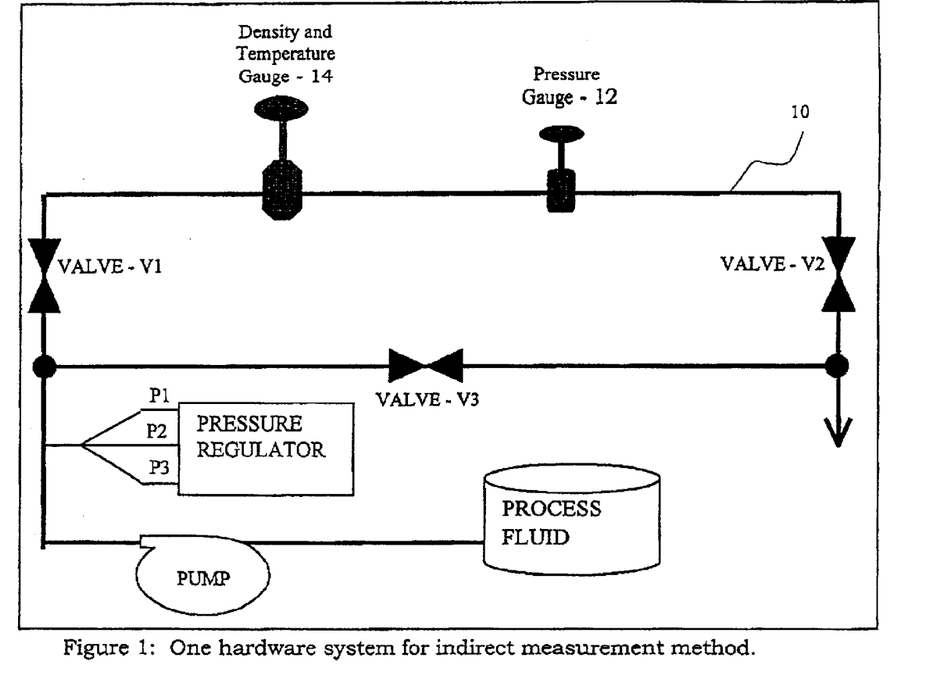
FIG. 1 is a schematic representation of an indirect measurement apparatus embodiment of the present invention (measuring density, calculating volume).

This method of indirectly determining air-free volume of liquid, and ultimately its true density, from the inverse of measured density, is demonstrated in FIG. 1. Such a device provides a simple method of obtaining the data required to calculate percent entrained air, percent dissolved air, Henry's Law constant, and true density of a solution in real-time.

The volume of free gas, $V_s$, at the standard conditions, in 1 unit of mass of liquid mixture is $$V_s = \left(\frac{1}{\rho_1} - \frac{1}{\rho_2}\right)\frac{T_s}{T}\frac{P_1^2}{P_s(P_2 - P_1)} + \left(\frac{1}{\rho_2} - \frac{1}{\rho_3}\right)\frac{T_s}{T}\frac{P_3(P_2 - P_1)}{P_s(P_3 - P_2)} + \qquad (38)$$
$$\frac{P_1 - P_s}{P_s}\left[\left(\frac{1}{\rho_1} - \frac{1}{\rho_2}\right)\frac{T_s}{T} - \left(\frac{1}{\rho_2} - \frac{1}{\rho_3}\right)\frac{T_s}{T}\frac{P_3(P_2 - P_1)}{P_1(P_3 - P_2)}\right]$$

The volume percentage of free gas, x %, at $P_s$ and $T_s$ can be calculated in the same manner as demonstrated in (34).

If even greater accuracy is required than that resulting from the preceding equations, the assumption upon which equation (25) is based can be eliminated. The solution for these key equations can then be found using iteration techniques. Such techniques are well known to those skilled in the art of deriving mathematical solutions to problems.

While the focus of the discussion in this application is often on "air", this invention can also be applied to the determination of amounts of any gas that is entrained and/or dissolved in any liquid. For instance, one important application of this invention is in the manufacture and processing of carbonated beverages, in which much more carbon dioxide gas than air is entrained and dissolved in the liquid carrier. Likewise, the present invention can be applied to processes conducted under an inert atmosphere, in which the gas may be nitrogen, helium, or another "inert" gas instead of (or in addition to) air.

U.S. patent application Ser. No. 09/893,883, now U.S. Pat. No. 6,496,781, entitled IMPROVED MIXTURE CONCENTRATION CONTROL IN MANUFACTURING PROCESSES, was filed on Jun. 29, 2001. Some (but by no means all) embodiments of the present invention can be used to make certain control methods described in that application even more accurate. Accordingly, the entire disclosure of that application is hereby expressly incorporated by reference.

EXAMPLES

Example 1

ENTRAINED AIR: Apparatus for the Indirect Measurement of Entrained and Dissolved Air Content in Liquids FIG. 1 depicts a particular hardware configuration that used the indirect measurement option described above. The apparatus of FIG. 1 takes measurements in a "no flow" state. Apparatus 10 of FIG. 1 includes a reservoir for process fluid, from which the fluid may be pumped by through piping which is under the control of a pressure regulator which is capable of setting at least three different pressures P1, P2, and P3 in the system. Each of these pressures may be either higher or lower than the preceding pressure. For instance, the measurement sequence could be P1<P2<P3, or P1>P2 and P1<P3, or any other combination. Also, these pressures may be set based on system constraints or testing objectives. Flow of the fluid in the piping is controlled by three valves V1, V2, and V3. This particular apparatus also includes a pressure gauge 12 and a density and temperature gauge 14.

A measurement procedure is carried out on apparatus 10 as follows. Valves V1 and V2 are opened to permit fluid pumped from the reservoir to fill the piping. Valve V3 is partially closed to ensure that measurement gauges 12 and 14 are filled with the fluid. The pressure regulator is set to P1 and valve V2 is closed to pressurize pressure gauge 12 to P1. Valve V1 is closed. Subsequently, pressure, temperature, and density data at pressure level P1 is collected until there is no longer any change in the data. (It is noted that initial changes in density and pressure result from air dissolving into or coming out of the fluid.) For the case where P1<P2<P3, the pressure regulator is set to P2 and valve V1 is opened to pressurize pressure gauge 12 to P2. Valve V1 is closed. Subsequently, pressure, temperature, and density data at pressure level P2 is collected until there is no longer any change in the data. Finally, the pressure regulator is set to P3 and valve V1 is opened to pressurize pressure gauge 12 to P3. Valve V1 is closed. Subsequently, pressure, temperature, and density data at pressure level P3 is collected until there is no longer any change in the data. The three sets of stabilized pressure, temperature, and density data may then be used in the processes of the present invention, which are described in detail hereinabove.

Example 2

ENTRAINED AIR: Optimizing Deaerator Operations in Coating Processes

Certain coating processing environments require that excessive entrained gases should be removed from the coating liquids prior to distributing the coating liquids onto the substrate. This is because entrained gas bubbles, especially larger ones, deteriorate coating quality and result in coating defects such as intolerable pinholes. Deaeration is therefore highly desirable where excessive entrained gas bubbles are presented. With the rapidly advancing technology of high-speed jet and curtain coating, in which thin liquid sheets are either injected or allowed to fall freely onto a substrate to be coated, any entrained large gas bubbles may even cause the breakdown of the integrity of the free coating liquid sheet. Thus, deaeration is a must for high-speed jet and curtain coating applications.

Figure 5:
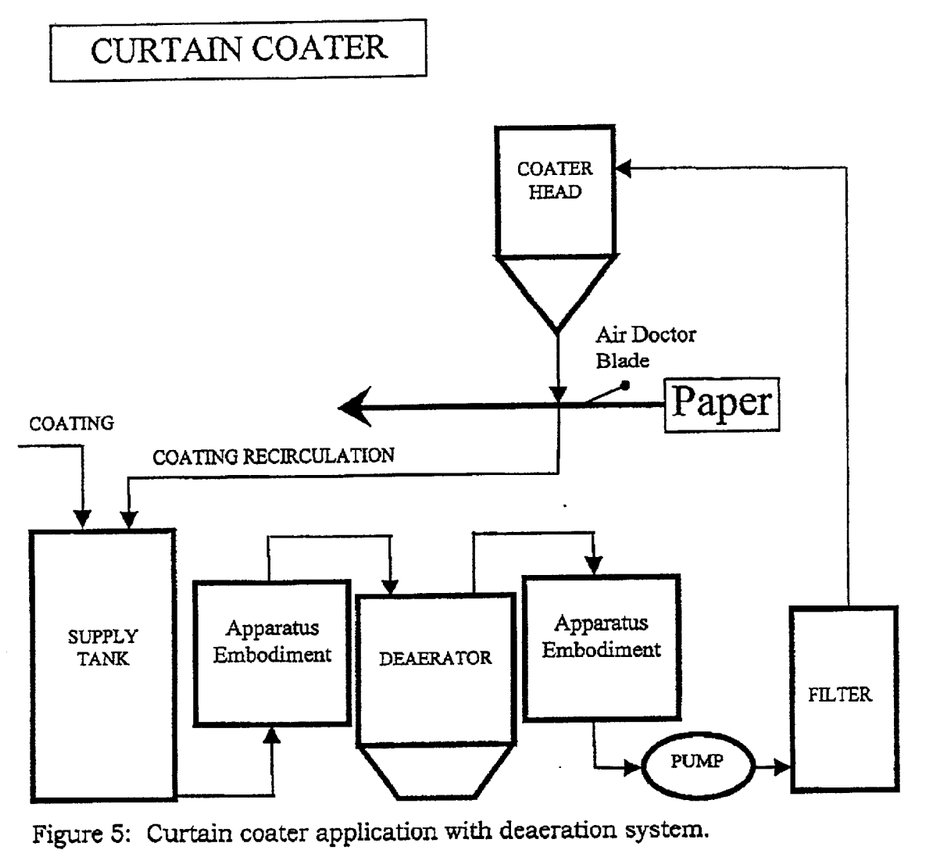
FIG. 5 is a schematic representation of a coating system including a deaeration module in accordance with this invention.

One application of the present invention, as depicted in FIG. 5, incorporates this invention both before and after the deaerator in a curtain coater piping system. The percent entrained air and percent dissolved air measurements provided before and after the deaerator unit improve the manufacturing process by enabling optimization of the deaerator unit, based upon determination of its process-specific deaeration efficiency. Process parameter adjustments (degree of vacuum, rotation speed of the deaerator, etc.) are made based upon the differences in "before" and "after" values. The output from the upstream apparatus embodiment is compared to that from the downstream apparatus embodiment to calculate the efficiency of air removal, and process parameters are changed to enhance the amount of air removed by the deaerator unit.

In addition to coating processes, other typical applications for deaerator systems include the packaging of ointments, creams, lotions, toothpaste, mayonnaise, ketchup, and lubricating grease.

Example 3

ENTRAINED AIR: Quality Control in Coating Application Systems

In Example 2, the deaerator units can be used to minimize waste costs due to the manufacture of off-quality product. When the level of percent entrained air that causes quality defects in a product is known, then the measured percent entrained air can be used to shutdown production, or can be monitored to predict when off-quality production may soon occur. It is not necessary to incorporate two (that is, "before" and "after") apparatus embodiments of this invention into processing systems (as illustrated in FIG. 5). Instead, the system could be configured with a single apparatus embodiment of this invention, located for instance after the deaerator unit. The system can then be configured to set off an alarm if too great a quantity of air bubbles are detected in the slurry downstream of the deaerator unit. With a processing system alarmed in this manner, the amount of expensive defoaming agent can be kept low, but can be immediately increased as soon as the alarm is triggered.

Also, since 100% deaeration is generally impracticable and unnecessary, an accurate measurement of the permissible maximum percent entrained air that the coaters can tolerate without causing noticeable quality problems enables controlling the coaters to run within acceptable operation windows.

As noted above, other typical applications for deaerator system improvements in accordance with this invention include—without limitation—the packaging of ointments, creams, lotions, toothpaste, mayonnaise, ketchup, and lubricating grease.

Example 4

TRUE LIQUID DENSITY: Percent Solids Control in Coating Substrates

One application of this invention is the on-line determination of the true density of a coating slurry applied to a substrate such as a paper web. The true density is then used to predict coating percent solids as described in U.S. patent application Ser. No. 09/893,883, IMPROVED MIXTURE CONCENTRATION CONTROL IN MANUFACTURING PROCESSES, referenced above. This coating percent solids data is then used to more efficiently control the application of the coating slurry onto the paper web. A significant processing benefit is realized due to the fact that percent solids is often the primary coating property affecting the quantity of coating being applied to the paper web. As the accuracy of the measurement of true density is improved, the accuracy of predicted coating slurry percent solids is improved. As the accuracy of coating slurry percent solids is improved, the control of the quantity of the coating slurry is also improved.

Paper coating slurries usually contain at least one and often all three of the following materials: pigments, binders, and additives. Generally, pigments constitute the main component of paper coating slurries. Pigments commonly used in current paper and board applications are kaolin clay, calcium carbonate, titanium dioxide, alumina trihydrate, synthetic and structured pigments, and so on. Binders normally constitute just a small part of paper coating slurries. Besides their role of binding, they also serve to fill up voids in the cellulose/pigment matrix. Natural binders include starch, soy protein, casein, while synthetic binders include styrene-butadiene latex, polyvinyl acetate latex, vinyl acrylic latex, polyvinyl alcohol, and so on. Although coating additives constitute only a small percent of paper coating slurries, they form a large, complex group with each serving a particular function. Coating additives include dispersants, viscosity modifier or water-holding agents, lubricants, crosslinkers or insolubilizers, biocides, pH control agents, repellents, optical brighteners, dyes, and foam control agents. This invention enables improved management of processes for applying any combinations of such materials.

Specifically, for a production environment in which the following production information is available to an on-line control system—1) the dry coating component ratio, 2) the relationship between the Additive Volume Coefficient of each coating component and the concentration of the component in the mixture, 3) the true density of each coating solid or solute component, and 4) the true density as determined in accordance with this invention—the following calculations are employed within the control system to determine the coating slurry percent solids:

Determine the true density of the coating slurry by means of the technique provided by the present invention;

Using that true density determination, estimate (more accurately) the coating slurry percent solids by the method described in U.S. patent application Ser. No. 09/893,883; and Employ the (more accurate) coating slurry percent solids estimate to optimize coater operations.

Broadly speaking, this specific embodiment of the present invention provides a method of monitoring a continuous coating of a substrate with solids delivered in a slurry of water. A first step in the present application comprises setting a target solids weight-% for the slurry. That is, in order to practice the present invention, one must determine what the solids weight-% in the coating slurry should be in order to provide a coated substrate having the desired properties. Having determined that target solids weight-%, one proceeds to provide a continuous industrial coating line with appropriate volumes of water and with appropriate amounts of the solid or solids with which it is desired to coat the substrate.

Figure 2:
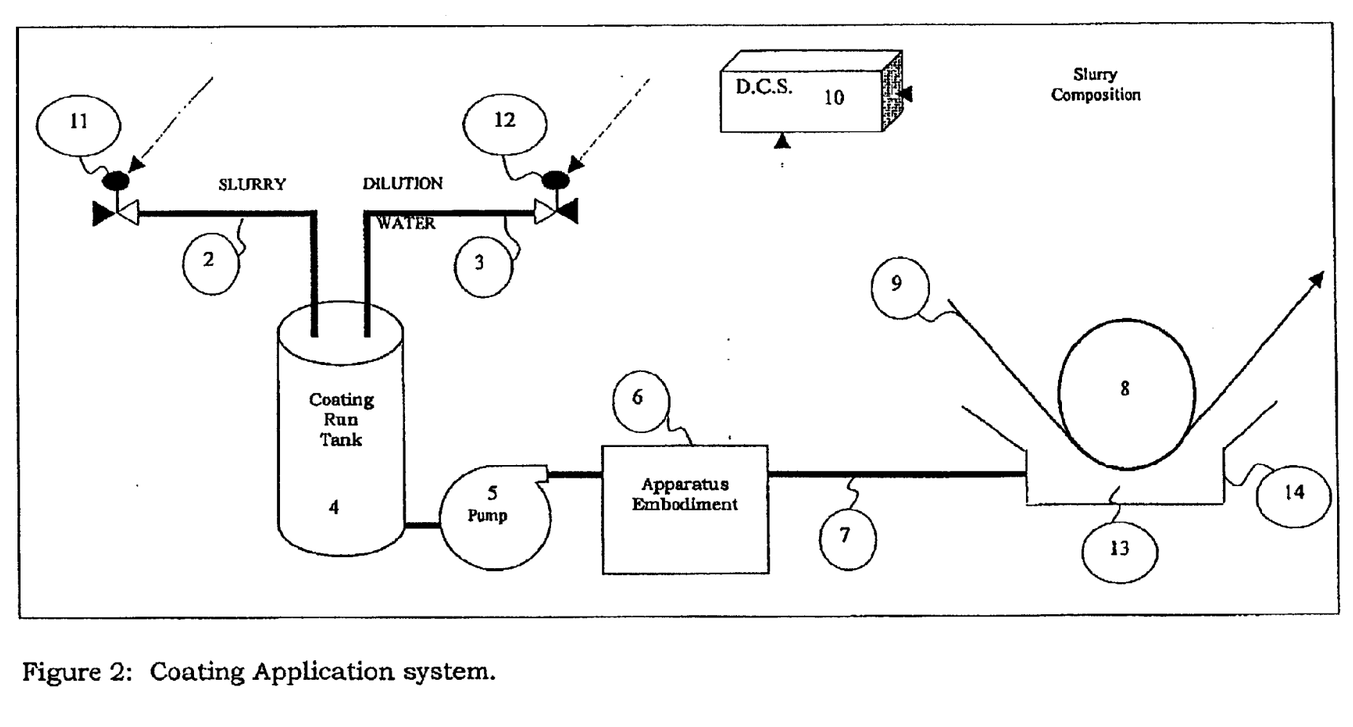
FIG. 2 is a schematic representation of an industrial coating line having an on-line measurement system in accordance with the present invention integrated into it.

In order to implement the present invention, one may modify a conventional industrial coating line by inserting an apparatus embodiment of the present invention into it. Referring to FIG. 2, industrial coating line 1 comprises coating run tank 4, pump 5, and coating slurry bath 14. These elements are linked by piping 7. A roll 8 is partially immersed in bath 14, and substrate 9 travels around the roll through the bath where it contacts coating slurry 13 (which includes a liquid carrier component). An apparatus embodiment of the present invention 6, along with the composition of the coating slurry, are fed as inputs into distributed control system 10. In accordance with the present invention, the distributed control system 10 converts these inputs to the true density of the coating. This true density is then converted into solids weight-% of the coating, making use of the procedure described in U.S. patent application Ser. No. 09/893,883, referenced above. This actual solids weight-% determination, in turn, is compared to the target coating solids weight-% for the slurry. If there is a difference, the distributed control system 10 adjusts coating inflows 2 and 3 with flow control valves 11 and 12 as appropriate to correct this difference.

This Example represents use in one particular paper coating process. However, those skilled in the art will realize that this invention can be applied similarly to virtually any other commercial coating methods and in any other process environments where information on true liquid density or % solids is desirable.

Example 5

TRUE LIQUID DENSITY: Improved Control of Syrup Makedown

Another application of this invention is the on-line determination of the concentration of sugars dissolved in water, commonly referred to as °Brix. This measurement is used to control the process of making syrup such as that used with canned fruit. Such a control provides the food manufacturer with the ability to control the product's sugar content. This provides the customer with a consistent taste over time, and/or the knowledge of a sugar content maximum, which is important to those with certain health conditions.

Current methods of measuring °Brix include converting the measurement of syrup density to °Brix. This can be done using long-standing conversion tables available in the public domain. When incorporated into a control system, these conversions can occur on-line, thus providing real-time °Brix measurement. However, the accuracy of the density measurement is often unsatisfactory due to the presence of air entrained in the syrup being measured. In such a case, incorporating an apparatus of embodying the present invention into a syrup piping system, as shown in FIG. 3, provides more accurate control of the finished product than can be achieved in the absence of this invention.

When used in conjunction with an on-line control system as described in Example 4, this invention provides a method for accurately converting density to °Brix by supplying measured density values having improved accuracy. The first step in this application comprises setting a target °Brix for the dilute syrup. Next, the flows of concentrated syrup and dilution water are controlled to maintain the dilute syrup at the targeted °Brix.

Figure 3:
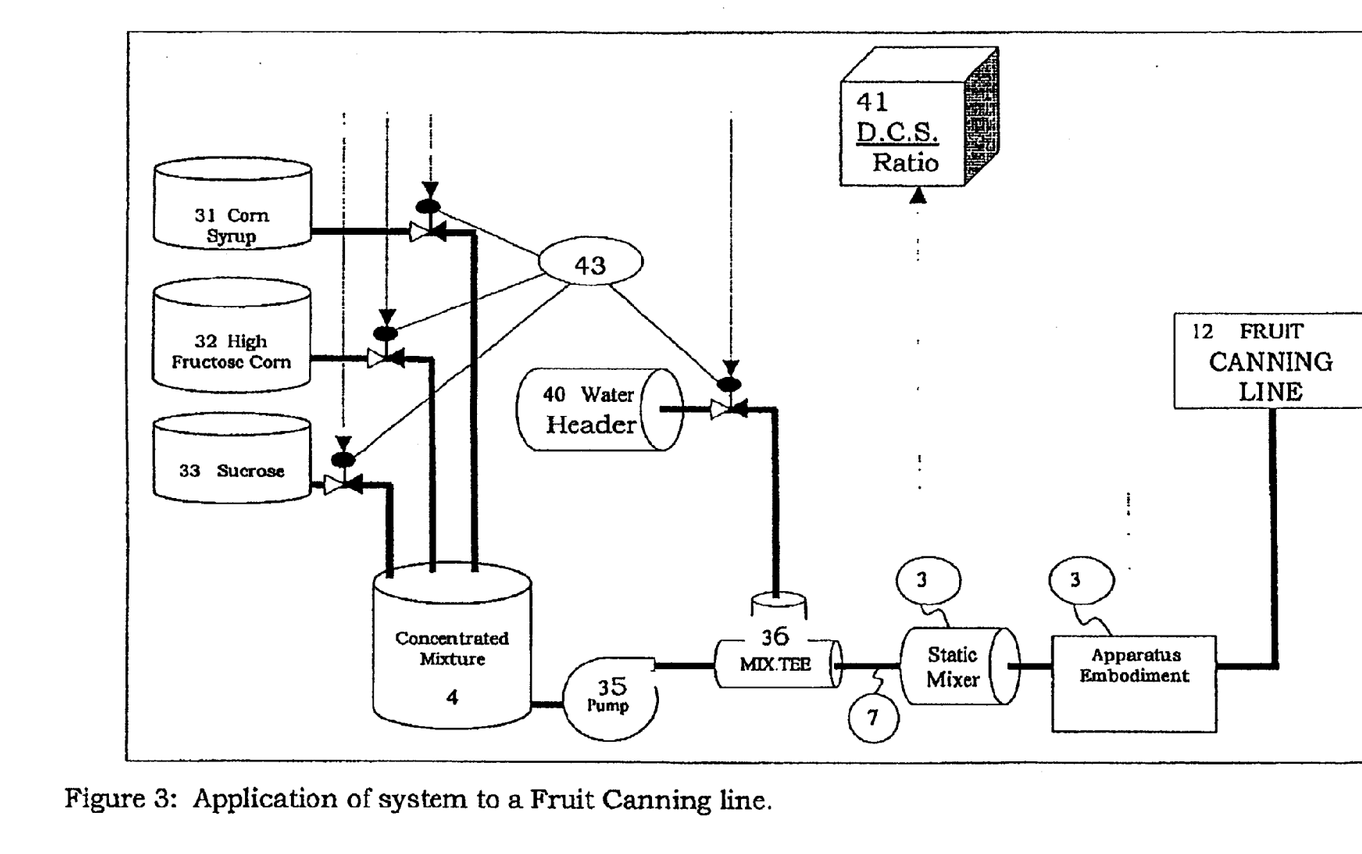
FIG. 3 is a schematic representation of a fruit canning line having a Distributed Control System operating in accordance with this invention.

Referring to FIG. 3, concentrated syrups 31, 32, and 33 are blended together as a concentrated mixture 4 in a ratio controlled by flow valves 43. The concentrated mixture travels through pump 35 to mixing tee 36 where it is blended with water from supply header 40. This dilute mixture travels through static mixer 38 to an apparatus embodiment of the present invention 39. The distributed control system 41 then converts the inputs to °Brix, making use of the air-free true densities of the dilute syrup provided by the application of this invention. This, in turn, is compared to the target °Brix. If a difference exists, the distributed control system adjusts the flow control valves 33 and 34 to correct the discrepancy.

Example 6

GAS CONTENT: Precise Control of Carbonation Level in Beverages

Still another application of this invention is a continuous process for preparing a carbonated beverage. In this Example, a quantitative target for a concentration of carbon dioxide, to be blended into an aqueous medium comprising water, high fructose corn syrup, caramel color, phosphoric acid, natural flavors, and caffeine, is set. Then carbon dioxide is continuously supplied to the aqueous medium in a vessel, and these components are mixed to form a carbonated aqueous medium in the vessel. As this process is being carried out, the total carbon dioxide concentration is determined by procedures set forth hereinabove. This calculated carbon dioxide concentration is continuously compared to the target carbon dioxide concentration. When the calculated carbon dioxide concentration is greater than or less than the target carbon dioxide concentration, the volume of carbon dioxide being supplied to the aqueous medium is lowered or raised, respectively.

In this type of application of the present invention, it is necessary to collect data at pressures lower enough than that corresponding to the target carbon dioxide concentration to cause some carbon dioxide to come out of solution. This is because all of the carbon dioxide is in the dissolved state at the target pressure, while the present invention requires the presence of entrained gases to be effective. The Direct Measurement Method is capable of operating at any pressure, including pressures below system pressures.

Example 7

GAS CONTENT: Test Results on Coating Slurries

| Test Result on Coating Slurry I | | | |
|---|---|---|---|
| Traditional Model | | New EAM Model | |
| Meas. Points | % gas | Meas. Points | % gas |
| $P_1$ & $P_2$ | 14.1%, 15.9% | $P_1, P_2, P_3$ | 13.8% |
| $P_1$ & $P_3$ | 14.6%, 18.4% | $P_1, P_3, P_4$ | 14.1% |
| $P_1$ & $P_4$ | 16.3%, 15.5% | $P_1, P_2, P4$ | 13.7% |
| $P_3$ & $P_4$ | 19.0%, 14.6% | $P_2, P_3, P_4$ | 14.8% |

| Test Result on Coating Slurry II | | | |
|---|---|---|---|
| Traditional Model | | New EAM Model | |
| Meas. Points | % gas | Meas. Points | % gas |
| $P_1$ & $P_3$ | 13.2%, 14.9% | $P_1, P_2, P_3$ | 12.4% |
| $P_3$ & $P_7$ | 16.2%, 18.6% | $P_5, P_6, P_7$ | 11.6% |
| $P_1$ & $P_7$ | 13.2%, 18.7% | $P_1, P_4, P7$ | 12.1% |
| $P_2$ & $P_6$ | 13.7%, 17.1% | $P_2, P_4, P6$ | 12.0% |

Test liquids: Conventional coating slurries containing pigment, binders, and coating additives. Meas. Points: A set of different combination of equilibrium pressure measurement points with a test sequence ($P_4<P_1<P_2<P_3$) for Coating Slurry I and a test sequence ($P_1<P_2<$. . . $<P_7$) for Coating Slurry II. Pressures were measured by a pressure sensor with an indirect measurement system as illustrated in FIG. 1 (the corresponding equilibrium apparent densities were also measured by a coriolis mass flow meter with the measurement procedure described in Example 1). % Gas: Air concentrations at the standard condition with different sets of pressure measurement points, which are calculated by plugging the measured equilibrium pressures and apparent densities into the old and new models, respectively.

Comparison I: The outputs of % gas within the same set of pressure measurement points for the old model do not agree with each other due to a violation of Boyle's law when it is used for entrained gas application. In contrast, there is only one output within the same set of pressure measurement points for the new model.

Comparison II: The above flaw indicates that the output of % gas from the old model is measurement-point-dependent. Taking a set of data points $P_2$ & $P_6$, for example, choosing $P_2$ as a reference point would calculate % gas to be 13.7% while choosing $P_6$ as a reference point would predict % gas to be 17.1% instead. This sort of discrepancy doesn't exist in the model of the present invention.

Comparison III: For the old model, the larger the pressure difference between the two points, the more the inconsistency of % gas outputs would be, e.g., the outputs from data set $P_1$ & $P_7$. This inconsistency doesn't occur for the new model provided by the present invention.

Comparison IV: There is also a significant variation of % gas between different sets of pressure measurement points for the old model. Overall, the output of % gas from the new model is much more consistent than that from the old model.

The invention being thus described, it will be evident that the same may be varied in many ways. Such variations are not to be regarded as a departure from the spirit and scope of the invention, and all such modifications as would be apparent to one skilled in the art likewise constitute a part of the present invention.

What is claimed is:

1. A method of determining the amount of gas in a liquid which comprises subjecting a mixture of an incompressible liquid sample and a compressible gas to at least three different equilibrium pressure states, measuring the temperature and volume of the mixture at each of the at least three pressure states, determining the changes in volume of the mixture between at least two different pairs of pressure states, and calculating the amount of said gas in said liquid sample by using the equation $$x\% = \frac{V_s}{V_s + V}$$

wherein V is the volume of the gas-free liquid in a sample chamber at ambient pressure and $V_s$ is determined by the equation $$V_s = \frac{\Delta V_1 T_s}{T} \frac{P_1^2}{P_s(P_2 - P_1)} + \frac{\Delta V_2 T_s}{T} \frac{P_3(P_2 - P_1)}{P_s(P_3 - P_2)} + \frac{P_1 - P_s}{P_s} \left[ \frac{\Delta V_1 T_s}{T} - \frac{\Delta V_2 T_s}{T} \frac{P_3(P_2 - P_1)}{P_1(P_3 - P_2)} \right]$$

wherein $P_1$, $P_2$, and $P_3$ are three different equilibrium ambient pressures, $P_s$ and $T_s$, are standard pressure and temperature, $\Delta V_1$ and $\Delta V_2$ are the volume difference of the free air measured at an equilibrium state between $P_1$ and $P_2$ and $P_2$ and $P_3$, respectively.

2. The method of claim 1, wherein said at least three equilibrium pressure states differ from one another at least to the extent that the three different volumes differ from one another by at least 0.1%.

3. The method of claim 1, wherein said at least three equilibrium pressure states differ from one another at least to the extent that three different apparent densities of said liquid differ from one another by at least 0.1%.

4. The method of claim 1, wherein said at least three pressure states differ from one another by at least 0.1 psi.

5. The method of claim 4, wherein said at least three pressure states differ from one another by at least 1 atmosphere.

6. The method of claim 1, wherein said determination of changes in volume is accomplished by measurement of volumes.

7. The method of claim 1, wherein said determination of changes in volume is accomplished by measurement of apparent densities.

8. A method in accordance with claim 1, for automatically controlling the output of a continuous process, wherein said liquid is a liquid carrier component containing entrained gas, the method comprising:

a.) setting a quantitative target for weight-% in the liquid carrier component of one or more solids to be mixed with said liquid component and/or for concentration in the liquid carrier component of one or more liquids to be mixed with said liquid component;

b.) continuously mixing said solids and/or liquids with the liquid carrier component;

c.) filling a measurement chamber with the blended mixture and allowing it to come to equilibrium;

d.) recording equilibrium temperature, $T_1$, the volume of a sample of the mixture, $V_1$, and first equilibrium pressure, $P_1$;

e.) increasing or decreasing the volume of the mixture in the sample chamber, allowing the fluid to come to equilibrium, and recording equilibrium temperature, $T_2$, sample volume, $V_2$, and second equilibrium pressure, $P_2$;

f.) again, increasing or decreasing the volume of the mixture in the sample chamber, allowing the fluid to come to equilibrium, and recording equilibrium temperature, $T_3$, sample volume, $V_3$, and third equilibrium pressure, $P_3$;

g.) determining the true density, $\rho$, by employing the formula $$\rho = \frac{m}{V}$$

wherein the mass, m, is the mass of the liquid mixture sample, and, the gas-free volume of the liquid mixture, V, and the volume percentage of free air or other gas, x %, are calculated from the formulas $$V = V_{t1} - \left[ \Delta V_1 \frac{P_1}{(P_2 - P_1)} + \Delta V_2 \frac{P_3(P_2 - P_1)}{P_1(P_3 - P_2)} \right]$$

and $$x\% = \frac{V_s}{V_s + V}$$

wherein $\Delta V_1$ is the volume difference of the free gas between $P_1$ and $P_2$, $\Delta V_2$ is the volume difference of the free gas between $P_2$ and $P_3$, $V_{t1}$ is the total volume of the liquid carrier component and gas entrained therein, and Vs is the volume of free air or other gas under standard conditions and is calculated from the formula $$V_s = \frac{\Delta V_1 T_s}{T} \frac{P_1^2}{P_s(P_2 - P_1)} + \frac{\Delta V_2 T_s}{T} \frac{P_3(P_2 - P_1)}{P_s(P_3 - P_2)} + \frac{P_1 - P_s}{P_s} \left[ \frac{\Delta V_1 T_s}{T} - \frac{\Delta V_2 T_s}{T} \frac{P_3(P_2 - P_1)}{P_1(P_3 - P_2)} \right]$$

wherein these variables are provided by the data collected in steps d.–f.), and standard conditions refer to $P = P_s = 1$ atm, $T = T_s = 273$ K;

h.) calculating the weight-% of solids and/or the liquid concentration in the mixture with the equation $$m = \frac{1}{\left(1 - \rho_L \sum_{i=1}^{n} \frac{k_i x_i}{(\rho_S)_i}\right)} - \frac{\rho_L}{\left(1 - \rho_L \sum_{i=1}^{n} \frac{k_i x_i}{(\rho_S)_i}\right)} \left(\frac{1}{\rho}\right)$$

wherein $\rho_L$ is the density of the liquid carrier component, $k_i$ is the Additive Volume Coefficient (AVC) for each solid or liquid, $x_i$ is the weight-% dry for each solid or the concentration for each liquid, $(\rho_s)_i$ is the density of each solid or liquid, and $\rho$ is the true density of the mixture;

i.) comparing the calculated weight-% solids or concentration to the target weight-% solids or concentration; and, j.) if the calculated weight-% solids or concentration is greater or less than the target weight-% solids or concentration, lowering or raising the amount of solids or liquids mixed in step b.).

9. A method in accordance with claim 1, for automatically controlling the output of a continuous process, wherein said liquid is a liquid carrier component containing entrained gas, the method comprising:
   a.) setting a quantitative target for weight-% in the liquid carrier component of one or more solids to be mixed with said liquid component and/or for concentration in the liquid carrier component of one or more liquids to be mixed with said liquid component to the liquid carrier component;
   b.) continuously mixing said solids and/or liquids with the liquid carrier component;
   c.) diverting a sample of the mixture from the main piping system into the sample measurement chamber and allowing the sample to come to equilibrium;
   d.) recording equilibrium temperature, $T_1$, equilibrium density, $\rho_1$, and first equilibrium pressure, $P_1$;
   e.) adjusting the pressure of the fluid in the sample chamber, allowing the fluid to come to equilibrium, and recording equilibrium temperature, $T_2$, equilibrium density, $\rho_2$, and second equilibrium pressure, $P_2$;
   f.) again, adjusting the pressure of the fluid in the sample chamber, allowing the fluid to come to equilibrium, and recording equilibrium temperature, $T_3$, equilibrium density, $\rho_3$, and third equilibrium pressure, $P_3$;
   g.) determining the true density, $\rho$, by employing the formula $$\rho = \frac{1}{V}$$

wherein the volume, V, is calculated from the formula $$V = \frac{1}{\rho_1} - \left[\left(\frac{1}{\rho_1} - \frac{1}{\rho_2}\right)\frac{P_1}{(P_2 - P_1)} + \left(\frac{1}{\rho_2} - \frac{1}{\rho_3}\right)\frac{P_3(P_2 - P_1)}{P_1(P_3 - P_2)}\right]$$

wherein these variables are provided by the data collected in steps d.–f.);
   h.) calculating the weight-% of solids and/or the liquid concentration in the mixture with the equation $$m = \frac{1}{\left(1 - \rho_L \sum_{i=1}^{n} \frac{k_i x_i}{(\rho_S)_i}\right)} - \frac{\rho_L}{\left(1 - \rho_L \sum_{i=1}^{n} \frac{k_i x_i}{(\rho_S)_i}\right)}\left(\frac{1}{\rho}\right)$$

wherein $\rho_L$ is the density of the liquid carrier component, $k_i$ is the Additive Volume Coefficient (AVC) for each solid or liquid, $x_i$ is the weight-% dry for each solid or the concentration for each liquid, $(\rho_s)_i$ is the density of each solid or liquid, and $\rho$ is the true density of the mixture;
   i.) comparing the calculated weight-% solids or concentration to the target weight-% solids or concentration; and,
   j.) if the calculated weight-% solids or concentration is greater or less than the target weight-% solids or concentration, lowering or raising the amount of solids or liquids mixed in step b.).

10. The method of one of claims 8 or 9 for continuously coating a substrate, which method comprises:
    a.) setting a quantitative target for weight-% of one or more solids to be coated onto a substrate;
    b.) continuously applying the solids to the substrate via a carrier fluid;
    c.) measuring the apparent density of the slurry;
    d.) determining the true density of the slurry;
    e.) calculating the weight-% of solids in the slurry in the manner recited in claim 8 or in the manner recited in claim 9;
    f.) comparing the calculated weight-% solids to the target weight-% solids; and,
    g.) if the calculated weight-% is greater or less than the target weight-%, lowering or raising the amount of solids applied in step b.).

11. The method of claim 10, in which the substrate is a paper web and the solids component comprises kaolin clay, calcium carbonate, titanium dioxide, or alumina trihydrate.

12. The method of one of claims 8 or 9 for controlling the output of a continuous process for preparing a syrup, which method comprises:
    a.) setting a quantitative target for a concentration of one or more carbohydrates and/or carbohydrate-containing liquids to be blended into a syrup;
    b.) continuously supplying the carbohydrate and/or carbohydrate-containing liquid and a dilution liquid to a vessel and mixing said liquids to form a slurry;
    c.) measuring the apparent density of the slurry;
    d.) determining the true density of the slurry;
    e.) converting this true density to the calculated carbohydrate concentration;
    f.) comparing the calculated carbohydrate concentration to the target carbohydrate concentration; and,
    g.) if the calculated carbohydrate concentration is greater or less than the target carbohydrate concentration, lowering or raising the amount of carbohydrates and/or volume of carbohydrate-containing liquids supplied in step b.).

13. The method of claim 12, in which carbohydrates comprising sucrose and carbohydrate-containing liquids comprising corn syrup and high fructose corn syrup are mixed with a dilution liquid comprising water.

14. A method in accordance with claim 1, for controlling the output of a continuous process for preparing a carbonated beverage, which method comprises:
    a.) setting a quantitative target for a concentration of carbon dioxide to be blended into an aqueous medium;
    b.) continuously supplying carbon dioxide to the aqueous medium in a vessel and mixing those components to form a carbonated aqueous medium in the vessel at a preset "bottling" pressure $P_0$, wherein $P_0$ is the produced "bottling" pressure inside a sealed carbonated beverage container, at which pressure all of the free carbon dioxide is dissolved into the aqueous medium;
    c.) diverting a carbonated aqueous medium sample from the vessel into a sample measurement chamber at the same "bottling" pressure $P_0$;
    d.) reducing the aqueous medium pressure from $P_0$ to first equilibrium pressure $P_1$ allowing the dissolved carbon dioxide to start to be released back to the aqueous medium in a free-bubble form;
    e.) reducing the aqueous medium pressure further from $P_1$ to second equilibrium pressure $P_2$ allowing a sufficient amount of the dissolved carbon dioxide to be released back to the aqueous medium in a free-bubble form;
    f.) measuring the change in volume of the carbon dioxide liquid mixture at an equilibrium state between $P_1$ and $P_2$;

g.) reducing the aqueous medium pressure further from $P_2$ to third equilibrium pressure $P_3$ allowing more dissolved carbon dioxide to be released back to the aqueous medium in a free-bubble form;

h.) measuring the change in volume of the carbon dioxide liquid mixture at an equilibrium state between $P_2$ and $P_3$;

i.) determining the volume of free carbon dioxide, $V_s$, in the carbonated aqueous medium at the standard condition using the equation $$V_s = \frac{\Delta V_1 T_s}{T} \frac{P_1^2}{P_s(P_2 - P_1)} + \frac{\Delta V_2 T_s}{T} \frac{P_3(P_2 - P_1)}{P_s(P_3 - P_2)} + \frac{P_1 - P_s}{P_s}\left[\frac{\Delta V_1 T_s}{T} - \frac{\Delta V_2 T_s}{T} \frac{P_3(P_2 - P_1)}{P_1(P_3 - P_2)}\right]$$

wherein $P_1$, $P_2$, and $P_3$ are three different equilibrium ambient pressures, $P_s$ and $T_s$ are standard pressure and temperature, $\Delta V_1$ and $\Delta V_2$ are the volume difference of the free carbon dioxide measured at an equilibrium state between $P_1$ and $P_2$ and $P_2$ and $P_3$, respectively;

j.) calculating the carbon dioxide concentration using the equation $$x\% = \frac{V_s}{V_s + V}$$

wherein $V_s$ is the volume of free carbon dioxide determined in i.] and V is the volume of carbonated aqueous medium in the sample chamber at a preset "bottling" pressure $P_0$ upon which no free bubble should present;

k.) comparing the calculated carbon dioxide concentration to the target carbon dioxide concentration; and, l.) if the calculated carbon dioxide concentration is greater or less than the target carbon dioxide concentration, lowering or raising the volume of carbon dioxide supplied in step b.).

15. The method of claim 14, in which the carbonated beverage is selected from the group consisting of soft drinks, beer, and carbonated wines.

* * * * *